(12) United States Patent
Piwonka-Corle et al.

(10) Patent No.: US 10,814,358 B2
(45) Date of Patent: Oct. 27, 2020

(54) FLOOR CLEANING DEVICE WITH DISINFECTION CAPABILITIES

(71) Applicant: KÄRCHER NORTH AMERICA, INC., Denver, CO (US)

(72) Inventors: Timothy Piwonka-Corle, Boulder, CO (US); Garrett Geer, Boulder, CO (US); Rylee Schauer, Loveland, CO (US)

(73) Assignee: KARCHER NORTH AMERICA, INC., Denver, CO (US)

( * ) Notice: Subject to any disclaimer, the term of this patent is extended or adjusted under 35 U.S.C. 154(b) by 326 days.

(21) Appl. No.: 15/892,803

(22) Filed: Feb. 9, 2018

(65) Prior Publication Data

US 2018/0221920 A1     Aug. 9, 2018

Related U.S. Application Data

(60) Provisional application No. 62/457,020, filed on Feb. 9, 2017, provisional application No. 62/489,794, filed on Apr. 25, 2017.

(51) Int. Cl.
  *A47L 11/40*     (2006.01)
  *B08B 3/10*      (2006.01)
  (Continued)

(52) U.S. Cl.
  CPC ............. *B08B 3/102* (2013.01); *A47L 11/29* (2013.01); *A47L 11/302* (2013.01); *A47L 11/4016* (2013.01); *A47L 11/4022* (2013.01); *A47L 11/4038* (2013.01); *A47L 11/4044* (2013.01); *A47L 11/4083* (2013.01); *A61L 2/025* (2013.01); *A61L 2/24* (2013.01); *B08B 3/08* (2013.01); *C02F 1/34* (2013.01); *C02F 1/36* (2013.01); *A47L 2601/02* (2013.01); *A61L 2202/16* (2013.01); *A61L 2202/17* (2013.01);
  (Continued)

(58) Field of Classification Search
  CPC .................... A47L 11/4069; A47L 11/4083
  See application file for complete search history.

(56) References Cited

U.S. PATENT DOCUMENTS 2,163,793 A    6/1939  Logan
2,717,237 A    9/1955  Rempel
(Continued)

FOREIGN PATENT DOCUMENTS

WO   WO 2007/137223   11/2007
WO   WO 2010/002974   1/2010

OTHER PUBLICATIONS

International Preliminary Report on Patentability for International (PCT) Patent Application No. PCT/US2015/017553, dated Aug. 22, 2019, 6 pages.

(Continued)

*Primary Examiner* — Michael D Jennings
(74) *Attorney, Agent, or Firm* — Sheridan Ross P.C.

(57) ABSTRACT

Methods and systems for cleaning floor surfaces are provided. In various embodiments, floor cleaning devices comprise enhanced cleaning and disinfecting capabilities. A clean fluid storage tank and a spent fluid storage tank are provided on-board the device. Means for creating cavitation bubbles to enhance cleaning are contemplated. Additionally, chemical agents and systems are contemplated for sanitizing surfaces as well as fluid that is captured or recaptured by the device.

19 Claims, 11 Drawing Sheets

(51) Int. Cl.
| | |
|---|---|
| *A47L 11/30* | (2006.01) |
| *B08B 3/08* | (2006.01) |
| *C02F 1/34* | (2006.01) |
| *C02F 1/36* | (2006.01) |
| *A61L 2/025* | (2006.01) |
| *A47L 11/29* | (2006.01) |
| *A61L 2/24* | (2006.01) |
| *C02F 1/76* | (2006.01) |
| *C02F 1/467* | (2006.01) |

(52) U.S. Cl.
CPC ......... *A61L 2202/25* (2013.01); *C02F 1/4674* (2013.01); *C02F 1/76* (2013.01); *C02F 2303/04* (2013.01); *C02F 2307/12* (2013.01)

(56) References Cited

U.S. PATENT DOCUMENTS

| | | | |
|---|---|---|---|
| 4,029,260 | A | 6/1977 | Herrick |
| 4,211,744 | A | 7/1980 | Boucher |
| 4,348,783 | A | 9/1982 | Swanson et al. |
| 5,558,252 | A | 9/1996 | Stapensea et al. |
| 6,171,558 | B1 | 1/2001 | Simpson |
| 6,635,178 | B2 | 10/2003 | Bowman et al. |
| 6,735,811 | B2* | 5/2004 | Field ........................ A47L 11/03 15/320 |
| 7,251,853 | B2 | 8/2007 | Park et al. |
| 7,392,566 | B2* | 7/2008 | Gordon ...................... A47L 5/30 15/319 |
| 8,156,608 | B2 | 4/2012 | Field et al. |
| 8,652,800 | B2 | 2/2014 | Walsh et al. |
| 8,769,763 | B2* | 7/2014 | Kloeppel ................. A47L 11/03 15/320 |
| 8,808,649 | B2 | 8/2014 | Ingber et al. |
| 8,828,680 | B2 | 9/2014 | Williams et al. |
| 8,966,693 | B2 | 3/2015 | Tucker et al. |
| 9,128,058 | B2 | 9/2015 | Walsh et al. |
| 9,327,255 | B2 | 5/2016 | Ito et al. |
| 9,357,895 | B2 | 6/2016 | Liefheit et al. |
| 9,380,920 | B2 | 7/2016 | Pollack |
| 9,504,212 | B2 | 11/2016 | Michael et al. |
| 9,555,408 | B2 | 1/2017 | Tan et al. |
| 9,737,187 | B2* | 8/2017 | Bantum ................. A47L 7/0023 |
| 2005/0246853 | A1 | 11/2005 | Pierce et al. |
| 2005/0283940 | A1* | 12/2005 | Hertrick ................. A47L 7/0028 15/320 |
| 2011/0219555 | A1 | 9/2011 | Field et al. |
| 2012/0047677 | A1* | 3/2012 | Paliobeis ................. A47L 11/34 15/320 |
| 2015/0165459 | A1* | 6/2015 | Venard ................... B05B 9/0403 239/71 |
| 2015/0216385 | A1* | 8/2015 | Bantum ............... A47L 11/4069 15/322 |
| 2015/0313435 | A1* | 11/2015 | Citsay ................... A47L 11/283 134/6 |
| 2016/0095489 | A1 | 4/2016 | Pedlar et al. |
| 2017/0304875 | A1 | 10/2017 | Shanahan et al. |
| 2018/0110389 | A1* | 4/2018 | O'Kane ............... A47L 11/4061 |

OTHER PUBLICATIONS

"Chlorine Dioxide," United States Department of Labor—Occupational Safety & Health Administration, No Date Available, accessed via https://www.osha.gov/dts/chemicalsampling/data/CH_226600.html, 2 pages.
"Independent Testing Summary," VitalOxide, No Date Available, 2 pages.
"Sodium Chlorite Chlorine Dioxide Generators," Occidental Chemical Corporation, Jan. 2015, 5 pages.
"Venturi Meter and Orifice Plate Lab Report," Green Mechanic, Nov. 20, 2016, accessed via https://www.green-mechanic.com/2016/11/venturi-meter-and-orifice-plate-lab.html, 9 pages.
"VitalOxide Label," VitalOxide, No Date Available, 1 page.
"White Paper: Chariot® iScrub 20 Chariot@ iScrub 20 Deluxe," Windsor, 2010, 8 pages.
Arrojo et al., "A parametrical study of disinfection with hydrodynamic cavitation," Ultrasonics Sonochemistry, vol. 15, No. 5, 2008, pp. 903-908.
Aseev et al., "Effect of Hydrodynamic Cavitation on the Rate of OH Radical Formation in the Presence of Hydrogen Peroxide," Russian Journal of Physical Chemistry A, vol. 88, No. 1, 2014, pp. 28-31.
Assanta et al., "Importance of mechanical action in a terminal disinfection process for decontamination of Clostridium difficile spores on hospital inert contact surfaces," International Journal of Infection Control, vol. 11, No. 3, 2014, 9 pages.
Badve et al., "Microbial disinfection of seawater using hydrodynamic cavitation," "Separation and Purification Technology," vol. 151, 2015, pp. 31-38.
Balasundaram et al., "Study of Physical and Biological Factors Involved in the Disruption of *E. coli* by Hydrodynamic Cavitation," Biotechnology Progress, vol. 22, 2006, pp. 907-913.
Benarde et al., "Kinetics and Mechanism of Bacterial Disinfection by Chlorine Dioxide," Applied Microbiology, vol. 15, No. 2, 1967, pp. 257-265.
Biwer et al., "Environmental assessment in early process development," Journal of Chemical Technology and Biotechnology, vol. 79, 2004, pp. 597-609.
Brennan, "Chapter 5: Cavitation," in Fundamentals of Multiphase Flow, 2009, Cambridge University Press, Cambridge, pp. 128-149.
Caldwell, "Mechanics of Movement: Mantis Shrimp," The Patek Lab, No Date Availble, accessed via https://pateklab.biology.duke.edu/mechanics-movement-mantis-shrimp, 2 pages.
Cha et al., "Bactericidal Efficacy of Vital-Oxide®, Disinfectant Solution Against Salmonella Typhimurium and Brucella Ovis," Journal of Food Hygeine and Safety, vol. 27, No. 1, 2012, pp. 504-554.
Cvetkovic et al., "Application of hydrodynamic cavitation in ballast water treatment," Environmental Science and Pollution Research, vol. 22, 2015, pp. 7422-7438.
Dancer, "Controlling Hospital-Acquired Infection: Focus on the Role of the Environment and New Technologies for Decontamination," Clinical Microbiology Reviews, vol. 27, No. 4, Oct. 2014, pp. 665-690.
Deshpande et al., "Are hospital floors an underappreciated reservoir for transmission of health care-associated pathogens?," American Journal of Infection Control, vol. 45, 2017, pp. 336-338.
Doan et al., "Clinical and cost effectiveness of eight disinfection methods for terminal disinfection of hospital isolation rooms contaminated with Clostridium difficile 027," Journal of Hospital Infection vol. 82, 2012, pp. 114-121.
Donskey, "Does improving surface cleaning and disinfection reduce health care-associated infections?," American Journal of Infection Control, vol. 41, 2013, pp. S12-S19.
Dunn et al., "Session 2:3 Interactions of Ultrasound and Microorganisms in Suspension," in Interaction of Ultrasound and Biological Tissues, 1972, Bureau of Radiological Health, Seattle, pp. 65-68.
Fortner, "Water Vapor Almost Busts Dam," Popular Science, Mar. 5, 2003, accessed via https://www.popsci.com/scitech/article/2003-03/water-vapor-almost-busts-dam, 2 pages.
Gashchin et al., "Features of Disinfection Kinetics of Water Containing *Escherichia coli* in Conditions of Hydrodynamic Cavitation," Journal of Water Chemistry and Technology, vol. 30, No. 5, 2008, pp. 567-575.
Gogate, "Cavitation: an auxiliary technique in wastewater treatment schemes," Advances in Environmental Research, vol. 6, 2002, pp. 335-358.
Gordon et al., "The Chemistry of Chlorine Dioxide," Progress in Inorganic Chemistry, vol. 15, 1972, pp. 201-285.
Guo et al., "The effect of cavitation bubbles on the removal of juvenile barnacles," Colloids and Surfaces B: Biointerfaces, vol. 109, 2013, pp. 219-227.
Hulette, "An Intervention to Reduce the Rate of Hospital-Acquired Acinetobacter Infections in an Urban Community Teaching Hospital," Metropolitan Nashville Hospital Authority, No Date Available, 1 page.

(56) References Cited

OTHER PUBLICATIONS

Hulette, "Surface Contamination of Outpatient Clinics Before and After Routine Cleaning," Meharry Medical College, Nashville, Tennessee, No Date Available, 1 page.

Ji et al., "Unsteady Numerical Simulation of Cavitating Turbulent Flow Around a Highly Skewed Model Marine Propeller," Journal of Fluids Engineering, vol. 133, Jan. 2011, 8 pages.

Jyoti et al., "Effect of cavitation on chemical disinfection efficiency," Water Research vol. 38, 2004, pp. 249-2258.

Koganti et al., "Evaluation of Hospital Floors as a Potential Source of Pathogen Dissemination Using a Nonpathogenic Virus as a Surrogate Marker," Infection Control & Hospital Epidemiology, vol. 37, No. 11, Nov. 2016, pp. 1374-1377.

Kurutkan et al., "An implementation on the social cost of hospital acquired infections," International Journal of Clinical and Experimental Medicine, vol. 8, No. 3, 2015, pp. 4433-4445.

Lemmen et al., "Distribution of multi-resistant Gram-negative versus Gram-positive bacteria in the hospital inanimate environment," Journal of Hospital Infection, vol. 56, 2004, pp. 191-197.

Maslak, "Combination of hydrodynamic cavitation and chlorine dioxide for disinfection of water," Engineering in Life Sciences, vol. 11, No. 4, Aug. 2011, pp. 350-358.

Mason et al., "Potential Uses of Ultrasound in the Biological Decontamination of Water," Ultrasonics Sonochemistry, vol. 10, 2003, pp. 319-323.

Mayfield et al., "Environmental Control to Reduce Transmission of Clostridium difficile," Clinical Infectious Diseases, vol. 31, 2000, pp. 995-1000.

McCarthy, "Hospital acquired infections are falling, CDC reports," The BMJ, vol. 350, No. h296, 1 page.

Mo et al., "Kinetics of the Preparation of Chlorine Dioxide by Sodium Chlorite and Hydrochloric Acid at Low Concentration," Chemical Engineering Transactions, vol. 46, 2015, pp. 49-51.

Moholkar et al., "Modeling of hydrodynamic cavitation reactors: a united approach," Chemical Engineering Science vol. 56, 2001, pp. 6295-6302.

Noszticzius et al., "Chlorine Dioxide Is a Size-Selective Antimicrobial Agent," PLoS ONE, vol. 8, No. 11, 2013, 10 pages.

Ozonek, "Chapter 6: The use of cavitation to aid the water treatment process and effluent decontamination," in Application of Hydrodynamic Cavitation in Environmental Engineering, 2012, Taylor & Francis Group, London, 26 pages.

Park et al., "Assessment of the Levels of Airborne Bacteria, Gram-Negative Bacteria, and Fungi in Hospital Lobbies," International Journal of Environmental Research and Public Health, vol. 10, 2013, pp. 541-555.

Perez et al., "Activity of selected oxidizing microbicides against the spores of Clostridium difficile: Relevance to environmental control," American Journal of Infection Control, vol. 33, No. 6, pp. 320-325.

Petkovsek et al., "Rotation generator of hydrodynamic cavitation for water treatment," Separation and Purification Technology, vol. 118, 2013, pp. 415-423.

Pillai et al., "Studies on process parameters for chlorine dioxide production using IrO2 anode in an un-divided electrochemical cell," Journal of Hazardous Materials, vol. 164, 2009, pp. 812-819.

Rudolf et al., "Characterization of the cavitating flow in converging-diverging nozzle based on experimental investigations," EPJ Web of Conferences, vol. 67, 2014, 6 pages.

Rutala et al., "Guideline for Disinfection and Sterilization in Healthcare Facilities, 2008," Center for Disease Control, 2008, 524 pages.

Rutala et al., "Efficacy of Different Cleaning and Disinfection Methods against *Clostridium difficile* Spores: Importance of Physical Removal versus Sporicidal Inactivation," Infection Control and Hospital Epidemiology, vol. 53, No. 12, Dec. 2012, pp. 1255-1258.

Scherba et al., "Quantitative Assessment of the Germicidal Efficacy of Ultrasonic Energy," Applied and Environmental Microbiology, vol. 57, No. 7, Jul. 1991, pp. 2079-2084.

Song et al., "Effect of Aqueous Chlorine Dioxide and UV-C Treatment on the Microbial Reduction and Color of Cherry Tomatoes," Horticulture, Environment, and Biotechnology, vol. 52, No. 5, 2011, pp. 448-493. Abstract Only.

Thorn et al., "Comparative Antimicrobial Activities of Aerosolized Sodium Hypochlorite, Chlorine Dioxide, and Electrochemically Activated Solutions Evaluated Using a Novel Standardized Assay," Antimicrobial Agents and Chemotherapy, vol. 57, No. 5, May 2013, pp. 2216-2225.

Thorn et al., "Electrochemically activated solutions: evidence for antimicrobial efficacy and applications in healthcare environments," European Journal of Clinical Microbiology and Infectious Diseases, vol. 31, 2012, pp. 641-653.

Wang et al., "Disinfection of bore well water with chlorine dioxide/sodium hypochlorite and hydrodynamic cavitation," Environmental Tehcnology, vol. 36, No. 4, 2015, pp. 479-486.

White et al., "A microbiological evaluation of hospital cleaning methods," International Journal of Environmental Health Research, vol. 17, No. 4, Aug. 2007, pp. 285-295.

Wright, "Cavitation of a Water Jet in Water," A thesis submitted to the faculty of Brigham Young University in partial fulfillment of the requirements for the degree of Master of Science, Apr. 18, 2012, 82 pages.

Xu et al., "Inactivation of Clostridium difficile in sewage sludge by anaerobic thermophilic digestion," Canadian Journal of Microbiology, vol. 62, 2016, pp. 16-23.

Xu et al., "Investigation of the Cavitation Fluctuation Characteristics of Venturi Injector," Fluid Dynamics Research, vol. 47, 2015, 13 pages.

International Search Report and Written Opinion for International (PCT) Patent Application No. PCT/US2018/017553, dated Apr. 24, 2018 6 pages.

\* cited by examiner

FLOOR CLEANING DEVICE WITH DISINFECTION CAPABILITIES

CROSS-REFERENCE TO RELATED APPLICATIONS

This U.S. Non-Provisional Patent Application claims the benefit of U.S. Provisional Patent Application 62/457,020, filed Feb. 9, 2017 and U.S. Provisional Patent Application 62/489,794, filed Apr. 25, 2017, the entire disclosures of which are hereby incorporated by reference.

FIELD

The present disclosure relates generally to floor cleaning equipment. More specifically, embodiments of the present disclosure provide for floor cleaning devices and related methods of use that are suitable for cleaning and disinfecting floor surfaces. In preferred embodiments, devices are provided that comprise the ability to scrub a floor surface and in doing so reduce the number of pathogens that are either on the floor surface or in the waste water tank which contains dirty water removed from the floor during the cleaning operation.

BACKGROUND

Cleaning surfaces in acute care environments often involves specialized procedures designed to disinfect the surface during or after the cleaning operation. These processes often focus on surfaces that are frequently touched by patients and healthcare workers. In acute care environments, the floor surfaces can also be heavily contaminated, but traditionally have not been considered an important source for pathogen dissemination because they are rarely touched. However, floors are in frequent contact with objects such as socks, slippers, and dropped items, such as call buttons or blood pressure cuffs, which are subsequently touched by the hands of the patient and staff.

Recently, a study has been performed that documents the spread of pathogen surrogates from the floor to other room surfaces to high touch surfaces in the room and even to adjacent rooms and nursing stations. See, for example, "Evaluation of Hospital Floors as a Potential Source of Pathogen Dissemination Using a Nonpathogenic Virus as a Surrogate Marker" by Sreelatha Koganti, MD et al. published in *Infection Control & Hospital Epidemiology*, November 2016, Vol. 37, No. 11, which is incorporated herein in its entirety by reference. This study demonstrated that a nonpathogenic virus inoculated onto floors in hospital rooms disseminate rapidly to the hands of patients and to high-touch surfaces inside and outside the inoculated room. It suggests that improved cleaning and disinfection of floor surfaces can help to reduce the number of Hospital Acquired Infections (HAIs).

Floor cleaning equipment that is designed to both clean and disinfect floor surfaces is well documented in the prior art. For example, U.S. Pat. No. 7,251,853, which is hereby incorporated by reference in its entirety, describes a robotic floor cleaner with a floor-disinfecting function that utilizes a commercially available ultraviolet lamp to disinfect floor surfaces. In addition to ultraviolet light, ozone has been used in cleaning equipment to disinfect floor surfaces, see for example U.S. Pat. No. 9,380,920 which is hereby incorporated by reference in its entirety, and describes a floor cleaning machine that includes a method for generating ozone and introducing it into the circulating water within the machine for the purpose of eliminating pathogens in that water.

The generation of ultraviolet light is relatively energy intensive, so that large batteries or a plug-in power source is required to generate light of sufficient intensity for a disinfection function. High-intensity ultraviolet light can also have a bleaching effect on color dyes, so that with repeated use the color of the treated floor area may change as compared to other untreated areas of the floor. Ozone, while an effective sterilizing agent, is also a hazardous substance that is covered by OSHA regulations at certain concentration levels. Cleaning workers exposed to this gas may be required to use personal protective equipment when cleaning the floors. Like ultraviolet light, ozone is also a strong bleaching agent that can change the color of materials that are exposed to it. Ozone circulating in a cleaning system will also degrade the plastic, pumps, and other materials within the equipment unless specialized and costly ozone resistant material is used to construct the machine. Given the urgent need to reduce HAIs and the limitations of the current technology, there is opportunity to bring new technology to the solution to this problem that may be intrinsically safer for cleaning workers, or that does not damage floors or equipment.

SUMMARY

Accordingly, there has been a long-felt and unmet need to provide systems, methods and devices for cleaning and disinfecting flooring and ground surfaces wherein the displacement and spread of pathogens, particulate, microbes, and similar materials is eliminated or reduced.

Embodiments of the present disclosure provide a cleaning device that is operable to clean and disinfect a floor surface, and/or clean a floor surface and disinfect the water or fluid that is returned to the machine from the floor surface after the cleaning operation, or any combination of the above listed operations. These techniques are described in relation to a floor-scrubber; however, it is specifically contemplated that they can be applied to a variety of cleaning equipment including stand alone or truck mounted carpet extractor machines, automatic and automated mops, and hand-held cleaning devices that clean using a fluid that is deposited on the surface to be cleaned. Embodiments of the present disclosure further contemplate enhanced safety aspects for users of machines, wherein fluid collected within or by a machine is sanitized to reduce exposure to those who may be handling the fluid or operating the machine(s) (i.e. servicing the machine, emptying fluid from the machine, etc.). It is further contemplated that the surface to be cleaned is not limited to floor surfaces, but may include carpets, upholstery, bedding, horizontal surfaces such as counters, tables and trays, and vertical surfaces such as cabinets, walls, doors, and other equipment. Certain embodiments of the present disclosure contemplate providing methods and systems that are suitable for cleaning in acute care environments. Acute care environments, at least as used herein, refer to hospital and similar settings including, but not limited to, emergency departments, intensive care, coronary care, cardiology, neonatal intensive care, and other areas. However, methods and devices of the present disclosure are not limited to use in acute care or hospital and similar settings and may be employed in various settings and environments.

Embodiments of the present disclosure also contemplate the use and properties of cavitation bubbles and their ability to clean and disinfect either surfaces or volumes of liquid.

Such embodiments contemplate the use of ultrasound and other methods and devices to create bubbles in a fluid (e.g. water) through a process called cavitation. As reported by F. Dunn and W. T. Coakley in "Interactions of Ultrasound and Microorganisms in Suspension" *Interactions of Ultrasound and Biological Tissues*, ed. J. M. Reid and M. R. Sikov, pp. 65-68, DHEW/FDA 73-8008, Rockville, 1973, which is hereby incorporated by reference in its entirety, these cavitation bubbles can lead to the disintegration of both pathogenic and non-pathogenic microorganisms in the fluid. These bubbles can also clean dirt and debris from a surface to which they are expelled.

In some embodiments, cavitation bubbles are produced by the shearing effect of a high-pressure water jet that is discharged within a liquid. Methods and devices for forming cavitation bubbles are shown and described by Michael Marshall Wright in a thesis submitted to the faculty of Brigham Young University, dated Apr. 18, 2012, and which is hereby incorporated by reference in its entirety. Various techniques shown and described by Wright are contemplated for use with embodiments of the present disclosure. In preferred embodiments of the present disclosure, the injection of a high-pressure stream into a body of fluid, or passing through a specially designed Venturi tube is used to create cavitation bubbles. Such a method is generally more efficient than alternative embodiments including, for example, creation of cavitation bubbles through the use of ultrasound.

In certain embodiments, a floor cleaning device is provided that comprises a device capable of producing a high-pressure stream of water, and injecting the high-pressure stream into a body of fluid. In some embodiments, the device is disposed within a fresh water tank, a waste water recovery tank, or in a central tank of a recirculating system. This high-pressure stream, when sprayed into water contained within the system produces cavitation bubbles which can be used to disinfect the water in the tank, and/or surface upon which the water is sprayed or applied. In addition, the fluid containing the cavitation bubbles can be deposited on the floor or surface to be cleaned for enhanced cleaning and disinfection thereof.

In yet another embodiment, a floor cleaning device is provided that is capable of producing a high-pressure fluid stream which can be injected into a volume (e.g. puddle) of water directly in front of a squeegee (for example), and wherein cavitation cleaning and disinfecting is accomplished directly on the floor surface.

Embodiments of the present disclosure contemplate use of various techniques and devices to produce cavitation bubbles. Such devices and techniques include, for example, injection of a high-pressure stream, one or more Venturi tubes or features, an ultrasonic device, a reciprocating device (e.g. propeller), an orifice plate, a circulating water channel, a hydrofoil, and/or other means for creating cavitation bubbles.

In some embodiments, the principles of the Venturi effect are employed within floor cleaning devices to generate cavitation bubbles within a fluid provided within a floor cleaning device. One or more Venturi tubes are provided within at least one fluid flow path, wherein a constriction is provided to alter the velocity and pressure of a fluid passing through the Venturi. As shown and described in more detail herein, preferred geometries of a Venturi tube are provided that cause a generation of cavitation bubbles within a fluid in the system. One or more pumps are provided within a device to direct an appropriate fluid flow rate through the at least one Venturi tube provided in the system.

In various embodiments, the present disclosure provides a floor cleaning device with a high-pressure nozzle or other injection means to inject a stream of high-pressure fluid into a reservoir or volume of fluid (e.g. a clean fluid storage tank provided on-board). The Applicant has found that the provision of cavitation bubbles provide for an effective cleaning means for removing dirt and contaminants, as well as killing or removing pathogens and bacteria from a surface. It is believed that the formation and subsequent collapse of these cavitation bubbles provides significant advantages for cleaning and may reduce or eliminate the need to clean with chemicals. Specifically, the present disclosure contemplates the provision of cavitation bubbles in cleaning devices and operations to remove soil and macro-scale dirt or debris, as well as contaminants and pathogens, such as *E. coli* and salmonella. The collapse of cavitation bubbles, which may occur at and/or be caused by contact with a surface, is known to create a suctioning effect, comprises the release of a relatively large amount of energy, and acts to remove dirt from contacted surfaces and to provide a level of disinfection to the surface.

Although cavitation bubbles generally comprise unstable elements, Applicant has discovered that cavitation bubbles comprise sufficient structural stability and the ability to remain present in a volume of fluid to provide sufficient time for cleaning operations. For example, Applicant has discovered that cavitation bubbles may be formed or created in a volume of fluid, and at least a portion of that fluid can be transported or conveyed to a cleaning area prior to the collapse of the bubbles. This allows for cavitation bubbles to be created at one region or portion of a cleaning machine, and thereafter conveyed to another area (e.g. a floor surface) for use in cleaning without significant loss of the cavitation bubbles. In various embodiments, devices and methods of the present disclosure comprise such features and arrangements. Such arrangements may be advantageous, as the creation of cavitation bubbles at or proximate to a surface to be cleaned poses a risk of causing damage to the cleaning surface. In certain embodiments, cavitation bubbles are provided at or proximal to a surface to be cleaned. For example, cavitation bubbles may be provided in a pool or puddle of fluid provided on a surface by way of an injection nozzle, a propeller, and/or an ultrasonic device. In preferred embodiments, however, it is contemplated that cavitation bubbles are formed in one component or portion of a cleaning machine (e.g. a clean fluid storage tank), and are thereafter conveyed to a surface to be cleaned and impacted by the cavitation bubbles. Such preferred embodiments provide a system with reduced risk of damage to the surface to be cleaned (such as may occur with the provision of a high-pressure nozzle adjacent or proximal to a surface).

In various embodiments of the present disclosure, cleaning machines are provided wherein a solution is prepared or provided with cavitation bubbles, and wherein the solution is applied to a surface to be cleaned, preferably within approximately ten seconds of the creation of the cavitation bubbles. Such embodiments include the ability and functionality to continuously provide a solution with cavitation bubbles, and wherein the solution is conveyed to a surface to be cleaned, preferably within approximately ten seconds of a creation of the bubbles.

Embodiments of the present disclosure contemplate methods and systems for the disinfection of surfaces during cleaning, or the disinfection of water that is returned from cleaned surfaces after cleaning. In various embodiments, techniques for accomplishing this disinfection involve electro-chemical modification of a known disinfecting chemical, such as enhancing the production of Chlorine Dioxide in a Sodium Chlorite solution such that it temporarily becomes a stronger disinfecting agent, which is effective against a wider variety of pathogens or can kill selected pathogens within a shorter contact time.

A method of producing Chlorine-free Chlorine Dioxide as a disinfectant from Sodium Chlorite using an electrochemical cell is described in U.S. Pat. No. 2,163,793 to Ogden and U.S. Pat. No. 2,717,237 to Rempel, which are hereby incorporated by reference in their entireties. The application of this method is not limited to the use of Sodium Chlorite as a pre-cursor, but is reportedly effective using any chlorite and the chloride of an alkali or alkaline earth metal.

In one embodiment, a floor cleaning device is provided with an electrochemical cell disposed within a fresh water tank, a waste water recovery tank, or in a central tank of a recirculating system. The electro-chemical cell is designed to promote a reaction between Sodium Chlorite and Sodium Chloride (salt) and create an enhanced Chlorine Dioxide disinfecting fluid. This disinfecting fluid is operable to be deposited on a floor or other surface, disinfect that surface, or it can be used to disinfect either the contents of the waste water recovery tank or the water stream in a continuously recirculating cleaning system.

There is also a need to safely and effectively render inert biological organisms that may be present on surfaces to be cleaned or in spent cleaning fluids, etc. An aqueous solution of chlorine dioxide, various alkyls, one or more various salts and tap water ("Aqueous Solution"), in appropriate and desired concentrations and with varying contact dwell times, can be quite effective in safely rendering inert all forms of biological organisms and microbes, present on surfaces or in fluids.

In a preferred embodiment of the disclosure, tap water can be approximately 99% of the Solution, with the chlorine dioxide being approximately 0.200% of the Solution, an alkyl comprised of dimethyl benzyl ammonium chloride being approximately 0.125% of the Solution, a second alkyl comprised of dimethyl ethyl benzyl chloride ammonium being approximately 0.125% of the Solution, and the remaining portion of the Solution being a salt, such as an inorganic, ionic or mineral salts, typically in solution. One off-the-shelf solution that contains many, but not all, of these chemicals is VitalOxide, produced by Vital Solutions, LLC.

A desired Aqueous Solution may be effective in safely rendering inert and thus harmless, mold spores, organisms that produce mildew, active allergens, viruses, bacteria, fungi and other microbes. The Aqueous Solution works in some situations by attacking the envelope that contains DNA, protein or other active material, breaching that envelope and subjecting the core material, i.e. proteins, to the Aqueous Solution, usually rendering those materials inert. This process is sometimes referred to as "lysing" a cell.

An appropriate Aqueous Solution may be produced in any number of various ways. For example, part or all the Aqueous Solution may be produced as a concentrate, with that concentrate being stored on board a cleaning machine and with the concentrate(s) being injected into a cleaning fluid prior to a final solution being injected upon a surface to be cleaned or directly added to a spent fluid tank (either empty or containing spent fluid). In other embodiments, each of the components of the Aqueous Solution could be kept in separate containers on board a cleaning machine, mixed in a dispensing line or in a dispensing container included on the cleaning machine, and dispensed onto a surface to be cleaned, into a spent fluid tank or into a clean fluid tank, as may be desired and is understood by a skilled artisan. In yet another embodiment, the Aqueous Solution could be produced in a cleaning closet or other remote location, and placed in known manner into the "fresh" cleaning tank of the cleaning machine. In that way, the Aqueous Solution will be supplied to both the surface to be cleaned and into the spent fluid tank upon recovery from the surface being cleaned. Any variation on these themes could be pursued and implemented by a skilled artisan and are deemed well within the skill level in the art. The place of production for the Aqueous Solution is, in the end, not critical, but can be informed by various product or environment design requirements.

As is known in the cleaning and sanitizing apparatus art, portable spray systems that include connecting hoses, appropriate valving and/or or metering valves for selectively mixing incoming aqueous streams and/or dry chemicals is generally known. One such system is shown in U.S. Pat. No. 4,029,260, which is incorporated herein by this reference. Another portable chemical mixing system is shown in U.S. Pat. No. 5,558,252, which is also incorporated herein by this reference. A further system known in the art focuses on microfluidic mixing of aqueous solutions, with U.S. Pat. No. 9,555,408 being incorporated herein in its entirety. Real time injector systems are also used in the cleaning and sanitizing art and one such system is disclosed in U.S. Pat. No. 9,504,212, which is incorporated in its entirety herein by this reference. It is also known in the art how to construct micro-chemical analysis devices, micro-mixing devices and micro-chemical analysis systems and such systems are shown in U.S. Pat. No. 9,327,255, which is hereby incorporated into this disclosure in its entirety by this reference. These and other systems are known in the art and can be utilized by a skilled artisan to facilitate the on-board chemical mixing technologies and strategies discussed above.

In another embodiment, the cleaning machine may preferably have an onboard microorganism diagnostic system that may be in communication with the spent fluid tank. The diagnostic system may be operative to monitor different types of microorganisms being collected by the cleaning machine and deposited into the spent fluid container. The total number of detected organisms could also be determined by the diagnostic system. The diagnostic system could then calculate, with the help of a microprocessor and onboard analytical capabilities, essentially in real time, the most effective form of Aqueous Solution for use with surfaces being cleaned and/or the most effective Aqueous Solution to be used to sterilize spent fluid being stored in the spent fluid tank. The diagnostic system may also, with the help of circuity communicating between the diagnostic system and the Aqueous Solution mixing system, can direct what chemicals should be mixed and in what proportions and what dwell time should be used to create the most desired Aqueous Solution for the then involved situation and to communicate to equipment on the cleaning machine just how long the Aqueous Solution should remain on a surface prior to collection, or remain in the spent fluid tank prior to moving the device to a new location, etc.

Systems for identifying and quantifying target microorganisms are known and could be modified by a skilled artisan to operate in a portable floor cleaning environment. For instance, U.S. Pat. No. 8,808,649 discloses how to identify various bacteria in fluid, with that patent being hereby incorporated in its entirety into this disclosure. Similarly, U.S. Pat. No. 9,128,058 discloses a method for separating, characterizing and identify microorganisms in a sample of fluid, and that patent too is hereby incorporated into this disclosure by this reference. A further prior art system useful in identifying microorganisms in a sample of fluid is U.S. Pat. No. 8,828,680, which is hereby incorporated by this reference. Another incorporated prior art reference is U.S. Pat. No. 8,652,800, which discloses a method for separating, characterizing and identifying microorganisms using spectroscopic measurements.

In various embodiments of the present disclosure, cleaning devices are contemplated as comprising a plurality of on-board fluid storage tanks for clean and/or spent fluids. In some embodiments, a first tank or volume is provided for housing clean fluids to be dispensed to a floor surface during a cleaning operation and a second tank is provided for receiving or collecting spent fluids (e.g. those that are recovered or drawn from a surface by a vacuum). It is further contemplated that some embodiments of the present disclosure that comprise at least two storage tanks further comprise features and systems wherein a spent fluid is capable of being treated and cleaned. For example, in some embodiments, it is contemplated that used fluid collected in a second tank may be cleaned or disinfected. Such cleaning processes are achieved through, for example, the application of an Aqueous Solution to the dirty fluid and/or the application of cavitation to the fluid.

It is specifically contemplated that although an Aqueous Solution, such as Vital Oxide, is most convenient to and readily obtained on the market, all or some of the components of such an Aqueous Solution may be added to one or more of the tanks of the cleaning machine when they are in a non-aqueous form. The addition of these components can be prior to filling the tank with water, or the component can be added directly to the aqueous fluid already present in the tank.

In further embodiments, it is contemplated that embodiments of the present disclosure provide for floor cleaning devices that comprise a single on-board fluid storage tank. In such embodiments, the fluid storage comprises the ability to house and dispense a clean fluid as well as receive and "clean" a used or dirty fluid. The used or dirty fluid, which is preferably collected by a vacuum device, is transferred back to the storage tank. The fluid is cleaned or disinfected by the provision and creation of cavitation bubbles created in the fluid before, during, and/or after it is provided in the tank. In addition to or in lieu of the application of cavitation bubbles, an Aqueous Solution or other cleaning agent may be applied to the re-collected fluid. The provision of a single tank in accordance with such embodiments provides for a machine of reduced sized, weight, and power requirements. Overall system efficiencies are improved wherein the machine itself comprises less mass and is required to house and transport less mass. Such devices are therefore simpler to manufacture and require less power from a battery system, thereby further reducing the weight and cost of such systems.

Embodiments of the present disclosure contemplate methods and systems utilizing a combination of hydrodynamic cavitation and chemical disinfectants, which is found to be more effective at killing pathogens than either technique alone. It should be recognized, however, that the present disclosure is not limited to such systems. For example, in some embodiments, a device comprising and utilizing only cavitation features is contemplated.

Various features, devices and methods are described herein. It should be recognized that these features, devices and methods are not mutually exclusive and that the combination of various disclosed concepts may be combined. For example, embodiments of the present disclosure contemplate the use of Venturi features, an electrochemical cell, and a storage tank for housing a cleaning chemical or treatment chemical, even if such a specific combination is not shown in the Figures.

The Summary is neither intended nor should it be construed as being representative of the full extent and scope of the present disclosure. The present disclosure is set forth in various levels of detail in the Summary as well as in the attached drawings and the Detailed Description and no limitation as to the scope of the present disclosure is intended by either the inclusion or non-inclusion of elements, components, etc. in this Summary. Additional aspects of the present disclosure will become more readily apparent from the Detailed Description, particularly when taken together with the drawings.

BRIEF DESCRIPTION OF THE DRAWINGS

Those of skill in the art will recognize that the following description is merely illustrative of the principles of the disclosure, which may be applied in various ways to provide many different alternative embodiments. This description is made for illustrating the general principles of the teachings of this disclosure and is not meant to limit the inventive concepts disclosed herein.

The accompanying drawings, which are incorporated in and constitute a part of the specification, illustrate embodiments of the disclosure and together with the general description of the disclosure given above and the detailed description of the drawings given below, serve to explain the principles of the disclosure.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

Figure 1:
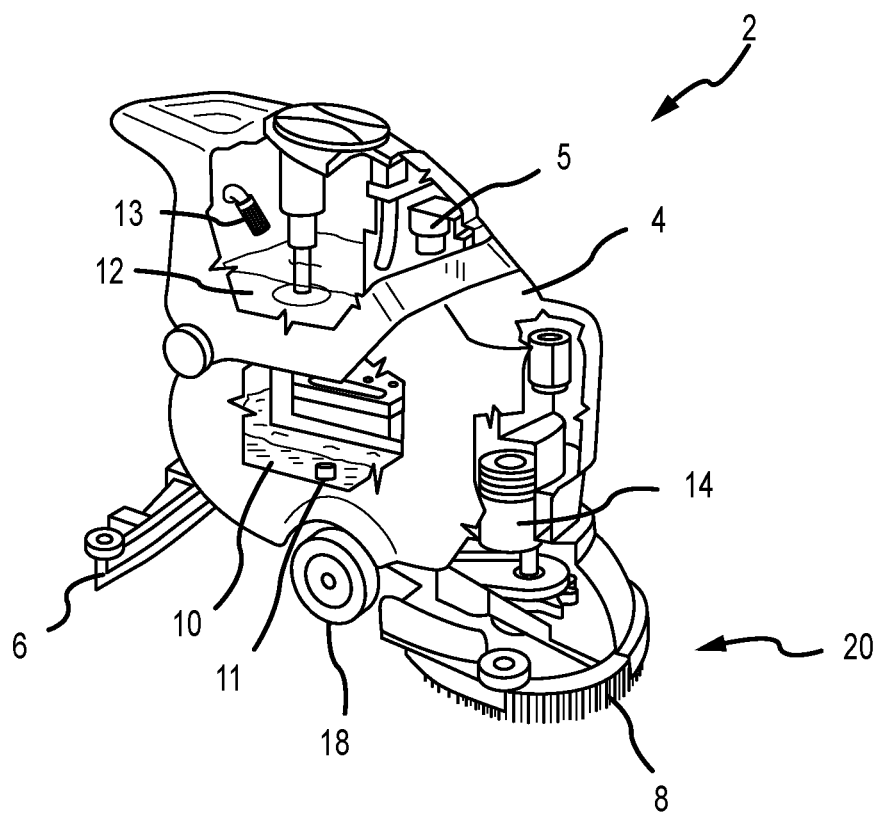

FIG. 1 is a perspective view of a floor cleaning device according to one embodiment of the present disclosure.

Figure 2:
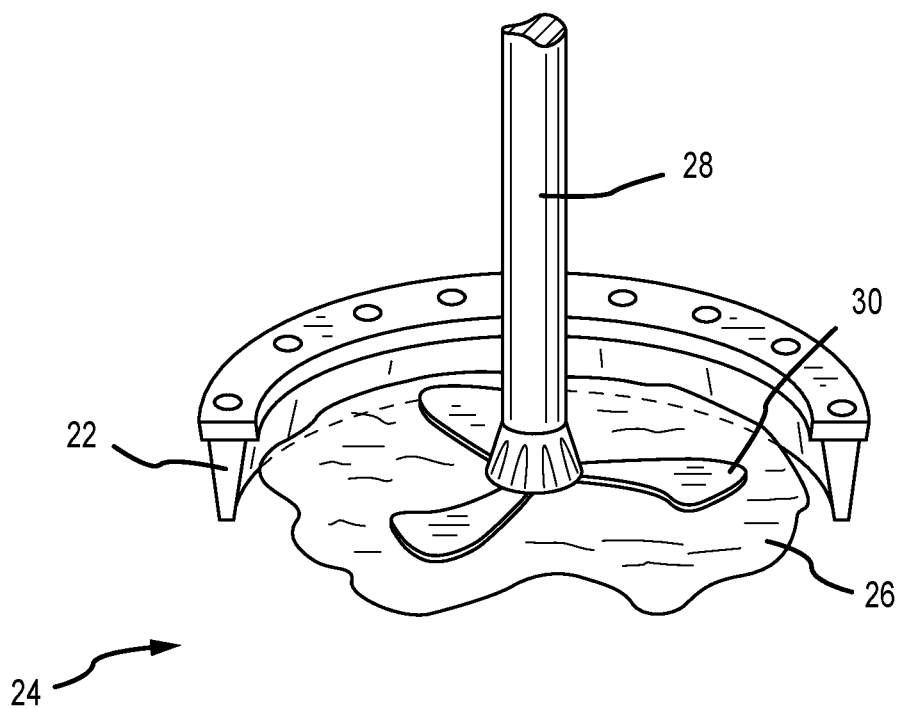

FIG. 2 is a perspective view of a component of a floor cleaning device according to one embodiment of the present disclosure.

Figure 3:
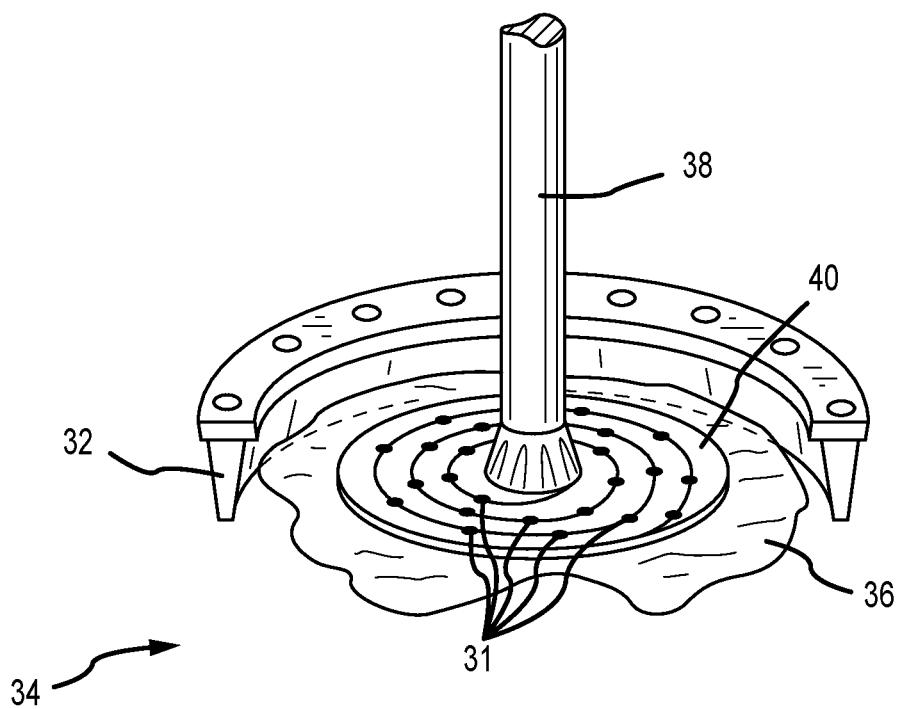

FIG. 3 is a perspective view of a component of a floor cleaning device according to one embodiment of the present disclosure.

Figure 4:
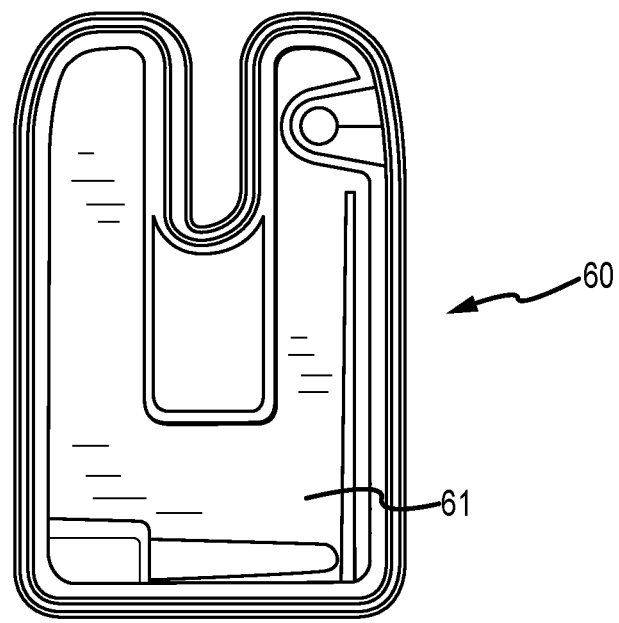

FIG. 4 is a top plan view of a tank feature of a floor cleaning device according to one embodiment of the present disclosure.

Figure 5:
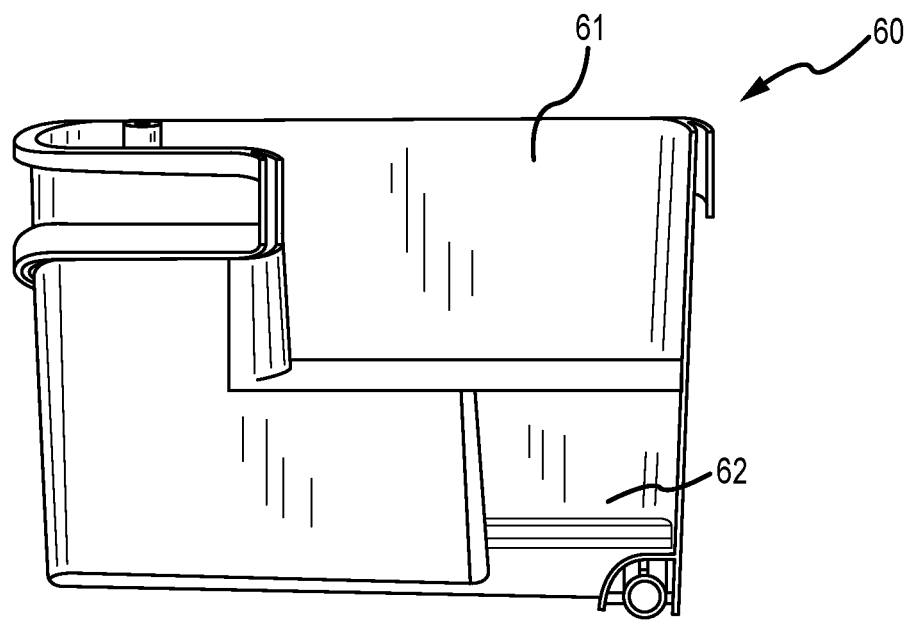

FIG. 5 is a cross-sectional elevation view of a tank system for a floor cleaning device according to one embodiment of the present disclosure.

Figure 6:
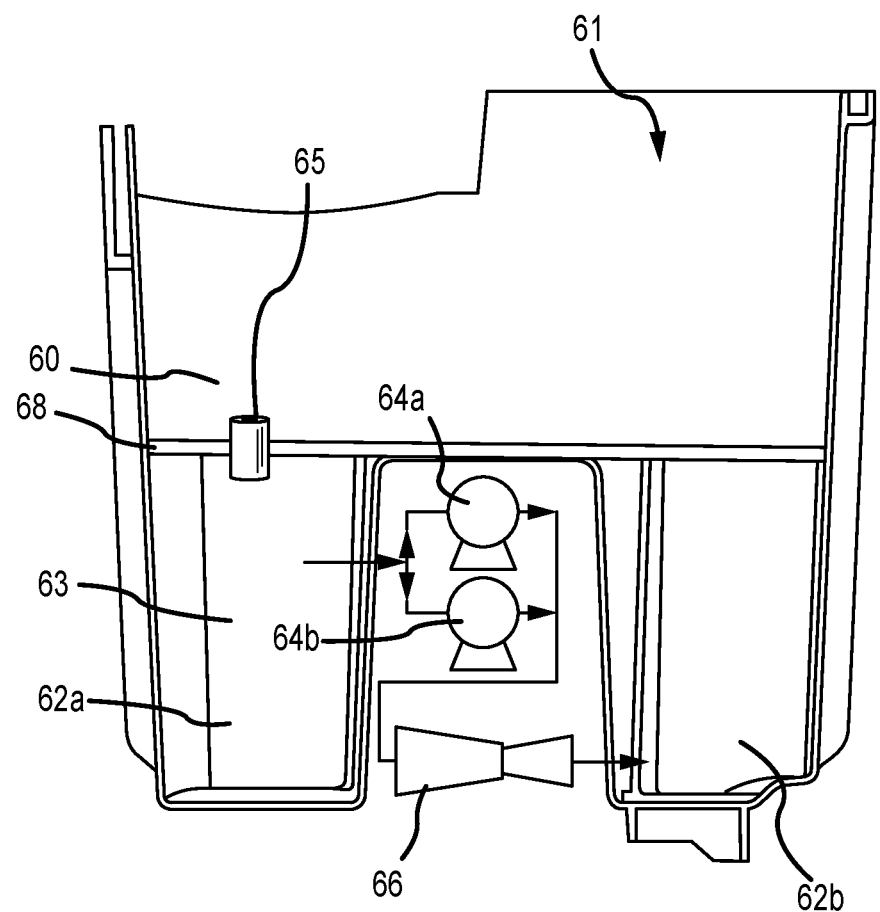

FIG. 6 is a cross-sectional elevation view of a tank system for a floor cleaning device according to one embodiment of the present disclosure.

Figure 7:
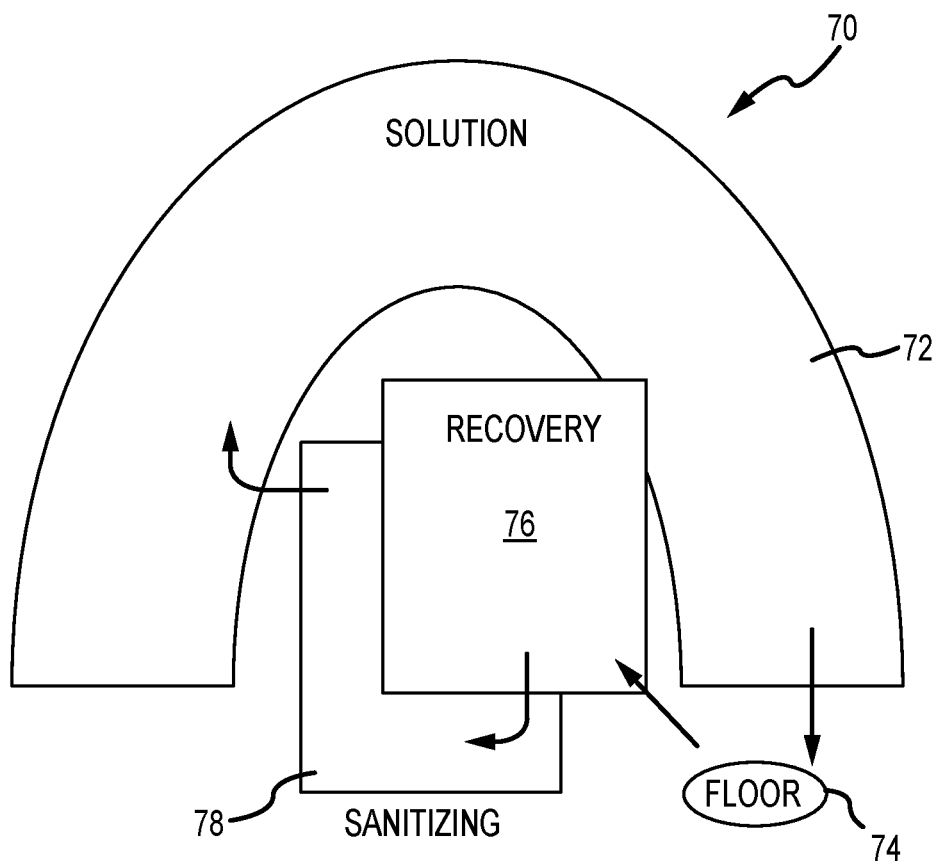

FIG. 7 is a schematic of a fluid recovery system and fluid flow path according to one embodiment of the present disclosure.

Figure 8:
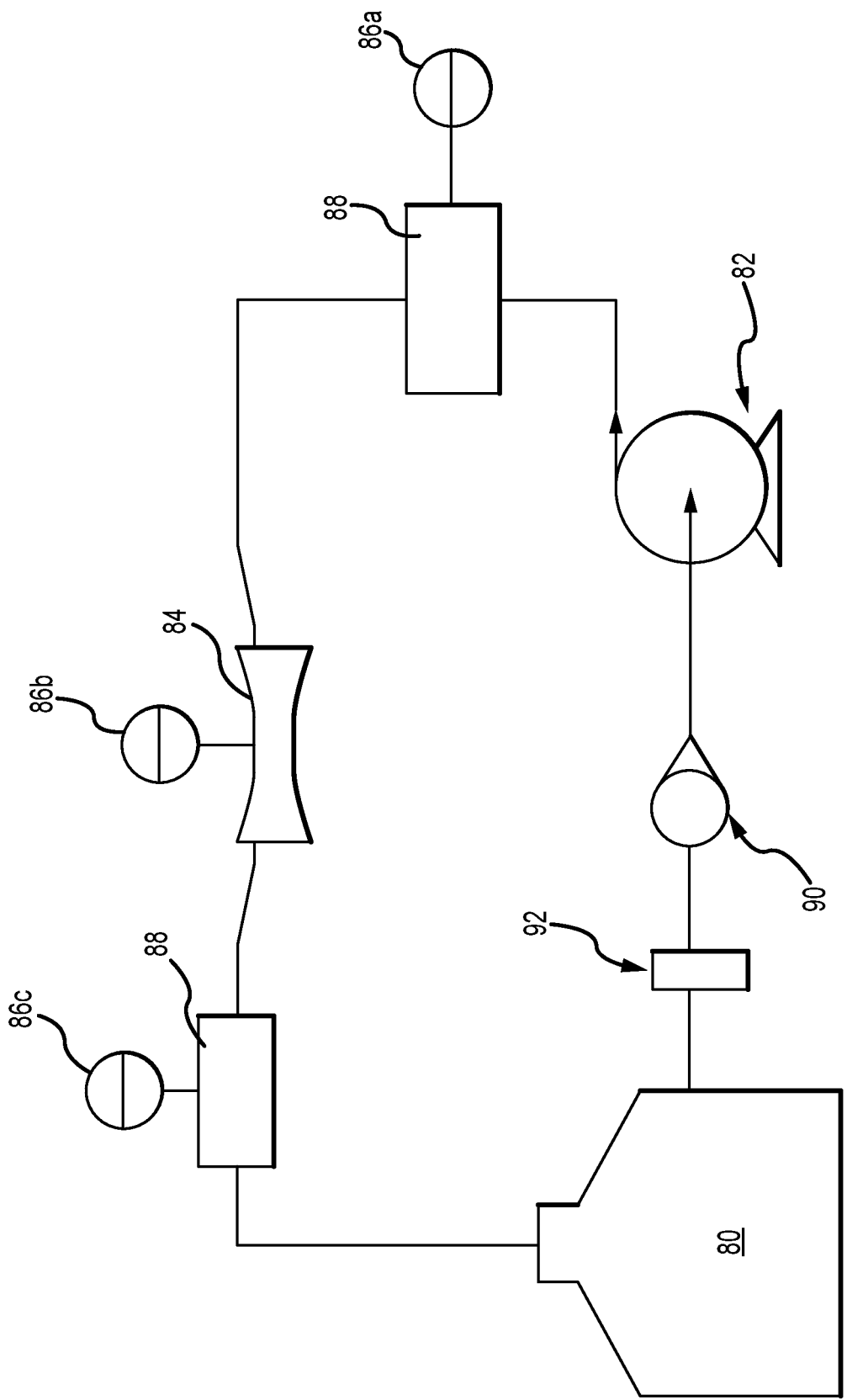

FIG. 8 is a schematic of components of a floor cleaning device according to one embodiment of the present disclosure.

Figure 9:
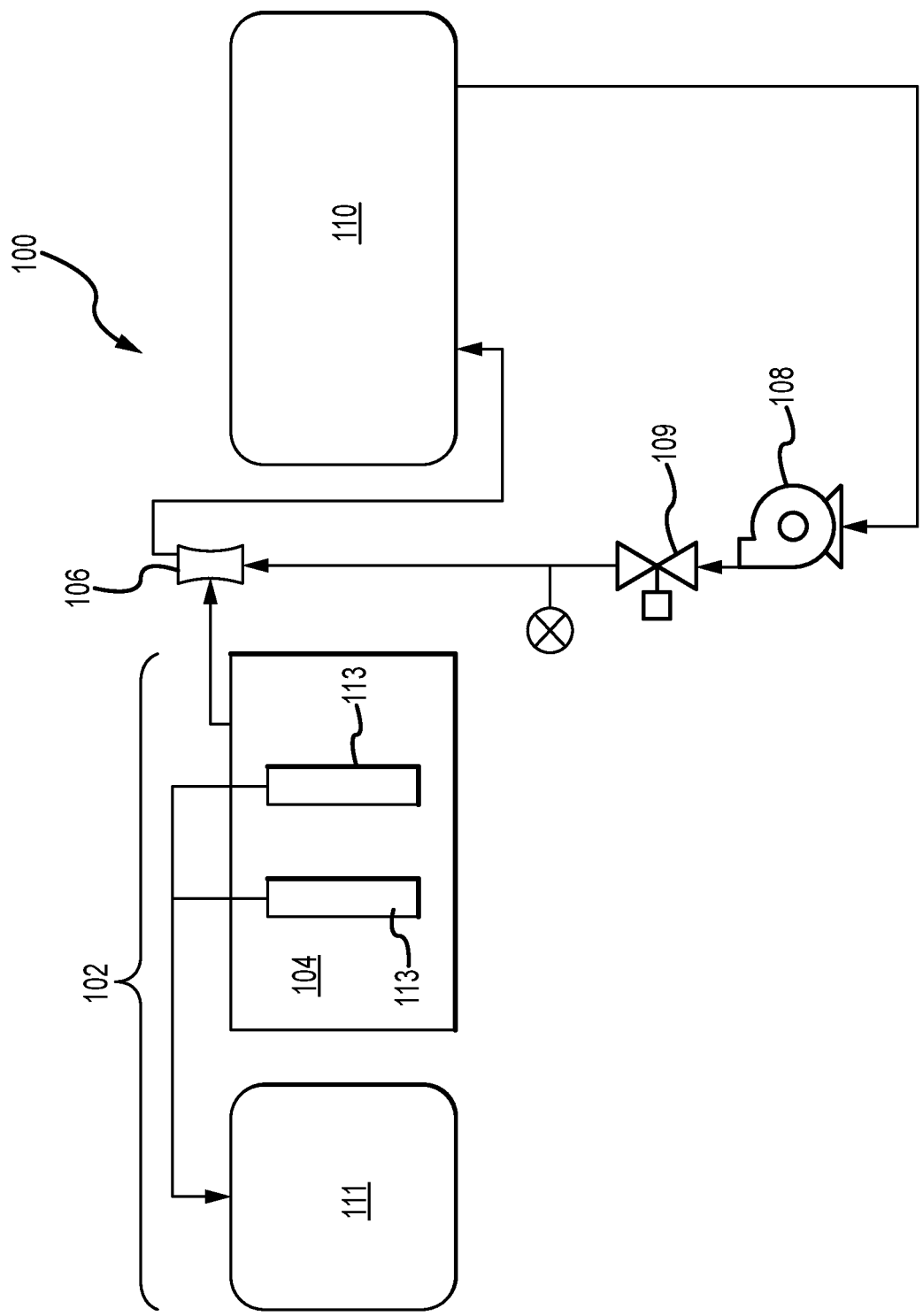

FIG. 9 is a schematic of components of a floor cleaning device according to one embodiment of the present disclosure.

Figure 10:
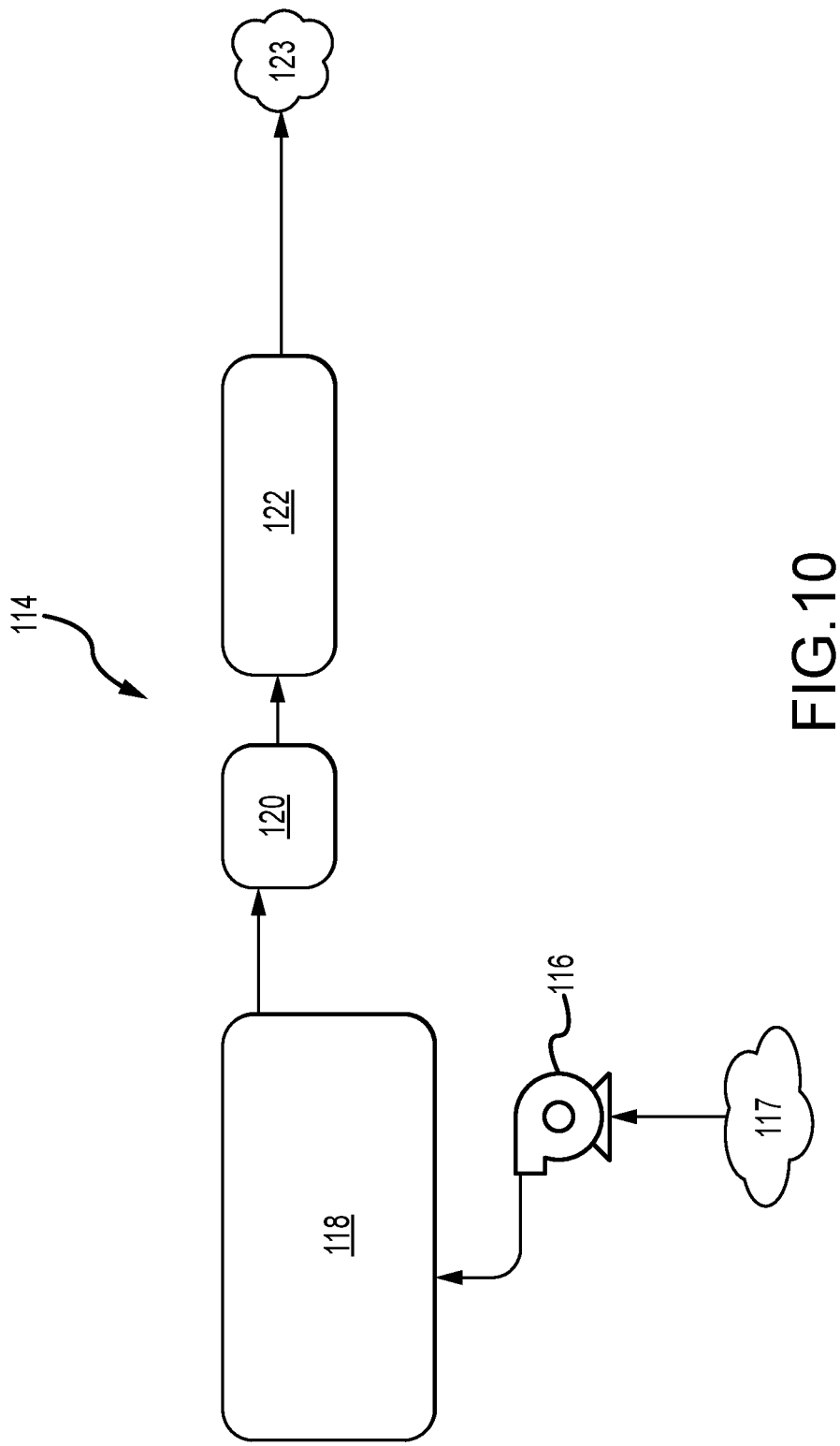

FIG. 10 is a schematic of components of a floor cleaning device according to one embodiment of the present disclosure.

Figure 11:
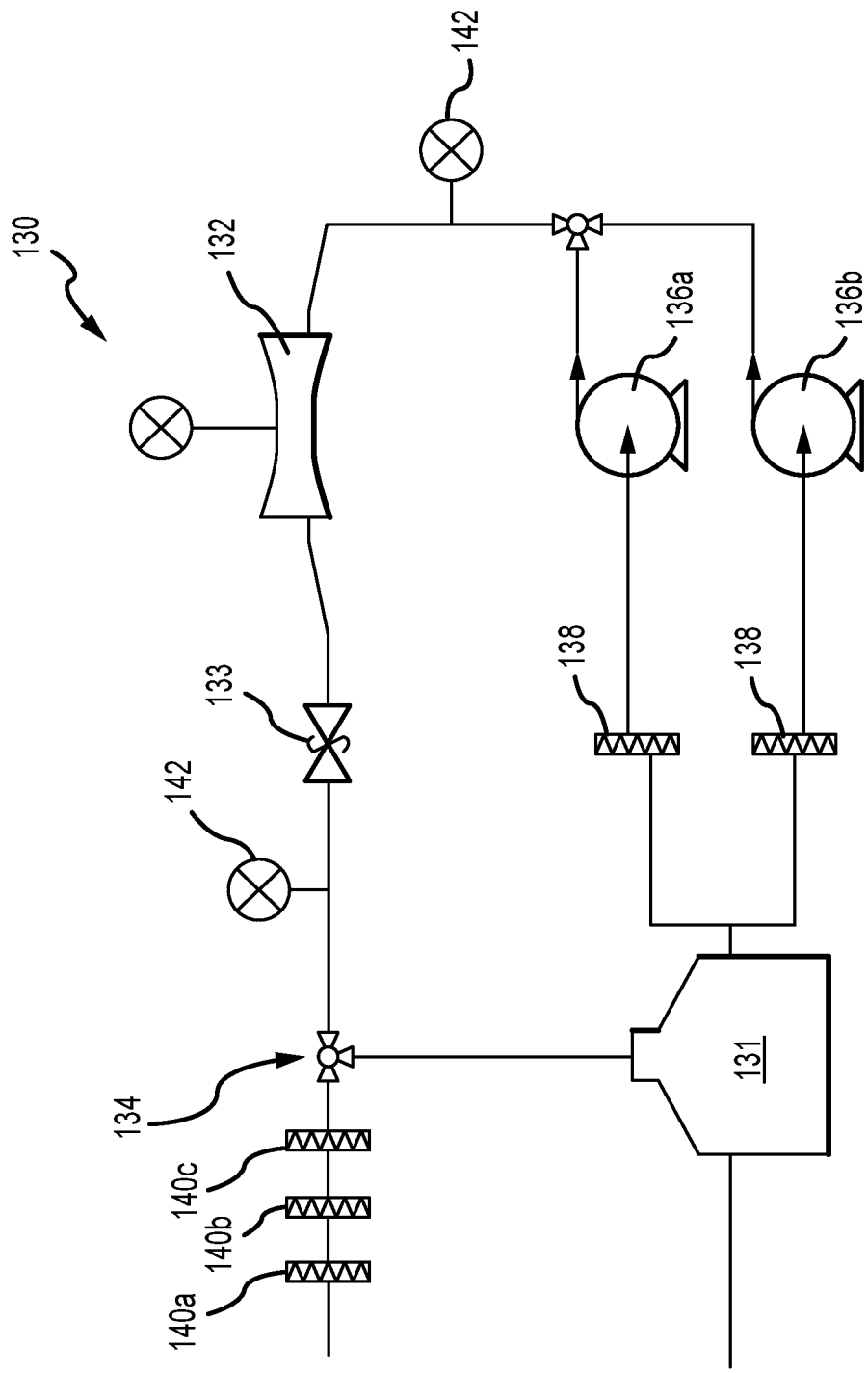

FIG. 11 is a schematic of components of a floor cleaning device according to one embodiment of the present disclosure.

Figure 12:
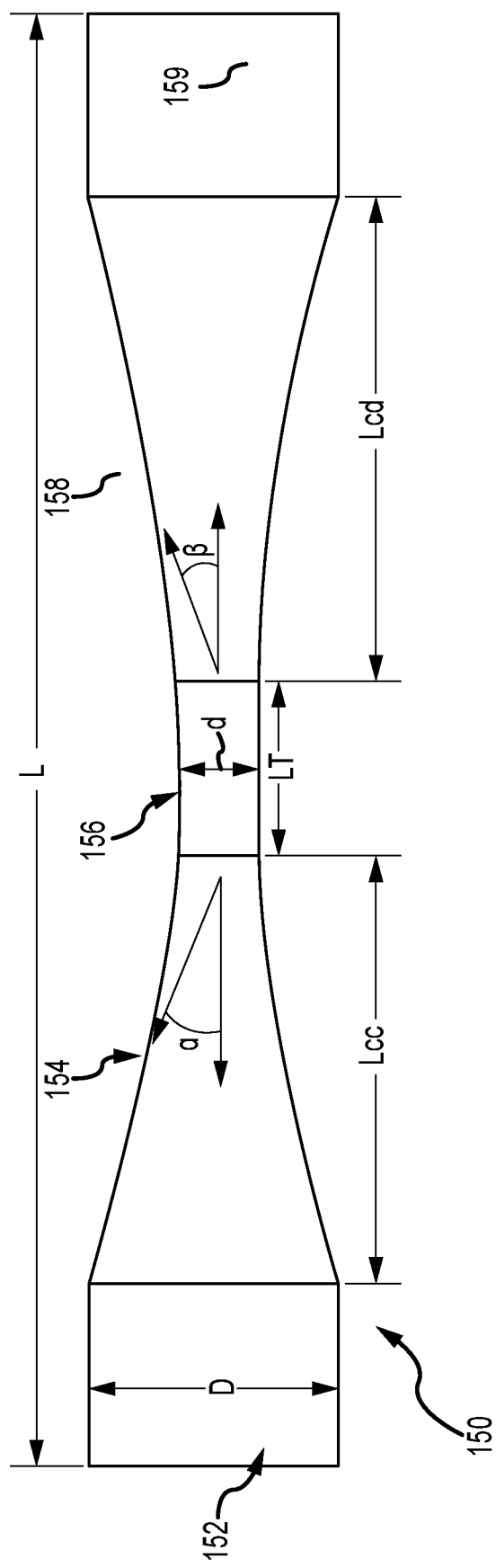

FIG. 12 is a schematic of a portion of a floor cleaning device according to one embodiment of the present disclosure.

DETAILED DESCRIPTION

FIG. 1 is a perspective view of a floor cleaning device 2 according to one embodiment of the present disclosure. The device 2 of FIG. 1 comprises a walk-behind cleaning device with a chassis 4, a trailing squeegee 6, and a brush or burnisher 8. It will be recognized, however, that the present disclosure is not limited to walk-behind floor cleaners. Various features and devices shown and described herein are useful with and contemplated as being provided without various different floor cleaners including, but not limited to, walk-behind and ride-on floor cleaners. The chassis 4 comprises an upper section and a lower section, and a first fluid storage tank 10 is provided in the lower section while a second fluid storage tank 12 is provided in the upper section. The brush 8 is powered by a motor 14, and a filter 13 is provided to filter fluid returned from the floor surface. In certain embodiments, a floor cleaning device 2 is provided wherein a second fluid storage tank 12 comprises a storage tank for a used or dirty fluid that may be filtered and/or disinfected and reused to clean a surface.

In various embodiments, cleaning devices 2 of the present disclosure provide a device wherein a first and/or second fluid storage tank 10, 12 comprises the ability to form cavitation bubbles in a fluid stored in the first fluid storage tank 10 (for example) prior to the dispensation of fluid to a surface to be cleaned. For example, and as shown in FIG. 1, the device 2 is contemplated as comprising a fluid injection nozzle in the form of at least one high-pressure injection nozzle 11 for injecting at least one high-pressure stream of fluid flow into a volume of fluid provided in the first fluid storage tank 10. The shear force created between the stored fluid and the injected fluid creates cavitation bubbles in the stored fluid, which may then be provided to a floor surface 20 to aid in cleaning operations. Stored fluid is provided to a floor surface 20 by various known means including, for example, one or more pumps to convey fluid from the tank to the floor 20 via a dispensing outlet or similar structure.

Various nozzles are contemplated for use with embodiments of the present disclosure. In preferred embodiments, it is contemplated that a floor cleaning device comprises at least one "zero degree" nozzle for injecting a direct jet of fluid into a preexisting volume of fluid at a pressure of between approximately 800 and 4000 psi and preferably of about 1,400 psi.

As further shown in FIG. 1, the device 2 comprises a second fluid storage tank 12 that is operable to receive and store a spent or dirty fluid. In the embodiment of FIG. 1, the device 2 comprises a vacuum motor 5 which is preferably provided in combination with a pick-up orifice proximal to the squeegee 6. The vacuum is operable to collect and convey fluid from the floor surface 20 to the fluid storage tank 12 where it is housed and/or treated. The second fluid storage tank 12 is contemplated as comprising fluid treatment systems, wherein fluid stored and housed by the tank 12 is treated and/or disinfected. Various embodiments of the present disclosure contemplate the provision of floor cleaning devices for use in acute care environments, and where pathogens are known or are likely to be present on a floor surface. Accordingly, in addition to removing and collecting dirt and debris from a floor surface, embodiments of the present disclosure contemplate devices that are also capable of trapping and killing pathogens, bacteria, and other potentially harmful organisms that may be present on a floor surface and/or that are collected by the device.

In some embodiments, an Aqueous Solution is provided as a concentrate on-board the device 2 and is injected into a cleaning fluid stored in the first solution storage 10 and/or the second solution storage tank 12. In other embodiments, components of the Aqueous Solution are kept in separate containers on board the device 2, and are mixed in a dispensing line or in a dispensing container included on the device 2, and dispensed onto a surface to be cleaned, into a spent fluid tank 12 or into a clean fluid tank 10. In yet another embodiment, the Aqueous Solution is produced in a cleaning closet or other remote location, and placed into the first fluid storage tank 10. In that way, the Aqueous Solution is supplied to both the surface to be cleaned 20 and into the spent fluid tank 12 upon recovery from the surface being cleaned. The present disclosure thus contemplates various embodiments wherein pathogens and similar harmful elements found on a surface to be cleaned are neutralized on contact and/or are contained and neutralized once collected within features of the device (e.g. the spent fluid storage tank 12).

Various embodiments of the present disclosure contemplate providing a volume of fluid on a floor surface. In some embodiments, it is contemplated that the volume of fluid is to be maintained on the floor surface (generally beneath the machine and in front of the squeegee) for a predetermined amount of time. For example, certain embodiments contemplate an extended use of fluid on a floor surface such that cavitation bubbles or chemical features of the fluid are provided with adequate time to perform their cleaning and/or sterilization functions. Therefore, as opposed to depositing and immediately collecting fluid, certain embodiments of the present disclosure contemplate employing features shown and described in U.S. Pat. No. 8,966,693 to Tucker et al., which is hereby incorporated by reference in its entirety. Tucker et al. discloses, for example, a squeegee and vacuum assembly with the provision of flow ports that allow for the collection and pick-up of dirty fluid, but also promote pooling of at least some fluid directly adjacent to the squeegee. Such features are specifically contemplated as being provided in various embodiments of the present disclosure, and are advantageous at least wherein fluid is to be maintained on a floor surface for a sufficient amount of time to allow for cavitation bubbles and/or chemical agents to perform cleaning functions and processes.

As is further shown in FIG. 1, a fluid recovery tank 12 is provided according to one embodiment of the present disclosure. In one embodiment, a floor cleaning machine is provided that comprises a plurality of tanks. Specifically, it is contemplated that floor cleaning machines of certain embodiments of the present disclosure comprise a recovery tank, a sanitizing tank, and a solution tank. The recovery tank comprises a storage volume (e.g. 5 gallons) that is operable to receive and store a liquid recovered or collected from a cleaned surface. A sanitizing tank is provided that comprises a temporary storage volume (e.g. 5 gallons) for sanitizing fluid received from the recovery tank. In some embodiments, the sanitizing tank comprises a recirculation line wherein fluid to be cleaned is cycled through a Venturi tube to create cavitation bubbles and enhance cleaning of the fluid. A solution tank is further provided that comprises a storage volume (e.g. 10 gallons) for storing fluid for use in cleaning by a scrubber, for example. FIG. 1 depicts a recovery tank 12 including a pick-up inlet 13 comprising a strainer or coarse-filter member. Although the embodiment of FIG. 1 illustrates a two-tank system, it is further contemplated that floor cleaning devices are provided that comprise a single tank system wherein fluid that is returned to the tank is cleaned in accordance with embodiments of the present disclosure.

FIG. 2 is a perspective view of a component of one embodiment of a floor cleaning device according to one embodiment of the present disclosure. As shown, a squeegee 22 is provided, which preferably comprises a vacuum shoe and pick-up orifice. The squeegee 22 preferably extends from a lower portion of the cleaning machine (not shown in FIG. 2) and contacts a floor or ground surface 24 and promotes or creates a pool 26 of cleaning fluid on the surface 24. A propeller 30 extends from a chassis of a cleaning machine wherein a drive shaft 28 is provided and comprises a propeller 30 at a distal end thereof. The drive shaft 28 supports the propeller 30 and is operable to provide a torque to the propeller 30, which comprises a plurality of blades to create a shear force on the fluid 26 provided on the floor surface 24. A shear force created by the propeller 30 is operable to create cavitation bubbles in the fluid 26 provided on the surface 24. The force of the propeller further provides for an agitation of fluid and a greater amount of fluid is provided in contact with a floor surface by way of the mixing and agitation thereof. In some embodiments, a propeller 30 is provided that is operable to generate turbulent flow in a fluid contacting the propeller 30, thereby enhancing cleaning properties of the device.

The cavitation bubbles are operable to enhance cleaning operations of the machine and fluid, as described herein. The embodiment of FIG. 2 depicts a propeller 30 provided on a drive shaft 28 that extends from a cleaning machine and wherein the propeller is operable to contact a fluid provided on a floor surface. In alternative embodiments, it is contemplated that a propeller is provided in a first fluid storage tank or a second fluid storage tank. The present disclosure contemplates creating and providing cavitation bubbles to a fluid in a dirty fluid storage tank and/or a clean fluid storage tank to clean or disinfect stored fluid or enhance cleaning abilities of a clean fluid, respectively. In such embodiments, the propeller is operable to create a shear force within a fluid stored within the first fluid storage tank and create cavitation bubbles in the fluid prior to dispensation of the fluid onto the floor surface.

In some embodiments, a floor cleaning device is provided that comprises at least one of a high-pressure injection nozzle and a Venturi tube in an outlet conduit or hose. For example, in some embodiments, a fluid dispensation conduit or hose for dispensing fluid from an internal storage tank to a floor surface comprises a high-pressure injection nozzle that is arranged and configured to create cavitation bubbles in a fluid as the fluid is being dispensed and/or just prior to dispensation of the fluid.

FIG. 3 is a perspective view of a component of one embodiment of a floor cleaning device according to one embodiment of the present disclosure. As shown, a squeegee 32 is provided, which preferably comprises a vacuum shoe and pick-up orifice. The squeegee 32 preferably extends from a lower portion of the cleaning machine (not shown in FIG. 3) and contacts a floor or ground surface 34 and promotes or creates a pool 36 of cleaning fluid on the surface 34. An acoustic generator extends from a chassis of a cleaning machine wherein a shaft 38 is provided and comprises an acoustic member 40. The shaft 38 supports the acoustic member 40 and is operable to provide a power to the acoustic member 40, which creates ultrasonic cavitation bubbles. The cavitation bubbles are operable to enhance cleaning operations of the machine and fluid, as described herein. The embodiment of FIG. 3 depicts an acoustic member 40 provided on a shaft 38 that extends from a cleaning machine and wherein the acoustic member is operable to contact a fluid provided on a floor surface. In alternative embodiments, it is contemplated that an acoustic member is provided in a first fluid storage tank (see 10 of FIG. 1, for example). In such embodiments, the acoustic member is operable to create a shear force within a fluid stored within the first fluid storage tank and create cavitation bubbles in the fluid prior to dispensation of the fluid onto the floor surface.

As shown in FIG. 3, a plurality of acoustic generator elements 31 are provided on a rotating disc or pad 40. The acoustic generator elements 31 are provided and arranged in a spiral pattern such that a rotation of the pad 40 causes a sweeping motion of each of the elements and a substantial entirety of a floor surface area beneath the pad is impacted by ultrasonic vibration.

FIGS. 4-5 are top plan and side elevation views of a tank for a floor cleaning device 60, respectively. The device 60 of FIGS. 4-5 comprises a plurality of internal fluid storage tanks including a recovery tank 61 and a sanitizing tank 62. The recovery tank 61 is provided vertically above the sanitizing tank and, in some embodiments, gravity-feeds fluid to the sanitization tank. One example of a gravity feed solution contemplated for use in embodiments of the present disclosure is shown in U.S. Pat. No. 9,357,895 to Leifheit et al., which is hereby incorporated by reference in its entirety. Features shown and described in Leifheit are contemplated as being employed in embodiments of the present disclosure to convey fluid from one tank to another within the device and/or to dispense fluid from the device to a floor surface. As shown in FIG. 5, the recovery tank 61 comprises a general collection tank for spent fluids. The sanitizing tank 62 comprises a compartment that is operable to house and selectively treat and disinfect fluid drained or transferred from the recovery tank 61.

FIG. 6 is a cross-sectional elevation view of a tank system 60 of a floor cleaning device of the present disclosure comprising a recovery tank 61 and a sanitization tank 62. The sanitizing tank 62 comprises a segmented storage volume at least partially interconnected by at least one pump 64. The number and sizing of pumps may be varied based on desired flow-rates and other considerations. In the depicted embodiment, the device comprises first 64a and second pumps 64b provided in parallel. The pumps and the segmented volume of the sanitizing tank 62 are provided with at least one Venturi tube 66 for creating a reduced pressure and inducing the creation of cavitation bubbles which are operable to clean and disinfect a solution passing through the Venturi. The sanitizing tank 62 of the depicted embodiment comprises a first volume 62a and a second volume 62b and wherein fluid is treated or sanitized upon passage or transfer from the first volume 62a to the second volume 62b. In some embodiments, fluid may be cycled through the Venturi 66 multiple times. The recovery tank 60 and the sanitization tank 62 are separated by a partition 68. Fluid may be transferred from the recover tank 61 to the sanitization tank 62 by various means including, but not limited to, a gravity-fed connection 65. Sanitized or partially-sanitized fluid may be pumped or otherwise transferred to a solution tank prior to dispensation to a floor or ground surface. In some embodiments, a plurality of pumps 136a, 136b are provided to achieve desirable conditions wherein the appropriate flowrate and pressures are achieved.

In some embodiments of the present disclosure, methods and systems are provided wherein a fluid is cycled or passed through a Venturi feature multiple times before the fluid is deemed ready for transfer to (or use in) a further process.

A method of operating the device of the embodiment of FIG. 6 is contemplated wherein a fluid is provided in the recovery tank 60. Fluid collected or provided in the recovery tank 60 is selectively transferred to a first volume 62a of the sanitization tank 62. In some embodiments, a valve or pump is selectively activated to enable flow from the recovery tank 60 to the first volume 62a. Subsequently, fluid is simultaneously transferred and sanitized by passing the fluid from the first volume 62a to the second volume 62b by pumping the fluid through the Venturi tube 66. Cavitation bubbles formed during the transfer process facilitate cleaning of the fluid and create for a fluid provided in the second volume 62b that comprises enhanced cleaning characteristics. The fluid in the second volume 62b is then operable to be transferred to a floor or other surface for use in cleaning operations.

FIG. 7 is a schematic of a batch system 70 for use with one embodiment of the present disclosure. As shown, the system 70 comprises a fluid flow path wherein a solution tank 72 is operable to store a fluid and to dispense the fluid to a floor or ground surface 74 for cleaning. The fluid may be ejected from the solution tank 72 either directly onto a floor or ground surface, or the fluid may be provided to a cleaning device (e.g. a brush or scrubber). A vacuum or other pick-up device (not shown) is provided to remove spent fluid from the ground or floor surface 74 and draw the fluid into a recovery tank 76. The recovery tank 76 is contemplated as comprising at least one filter provided at an entrance or exit to the recovery tank 76 or at a location provided therebetween. The recovery tank is in fluid communication with a sanitization tank 78 for sanitizing a collected fluid by one or more of the devices and methods described herein. The sanitizing tank 78 is in fluid communication with the solution tank 72 to return cleaned or sanitized fluid to the solution tank 72 for further use in floor cleaning operations. In preferred embodiments, the solution tank 72 comprises a tank provided at the lowest point of gravitational potential energy with respect to the sanitization tank 78 and the recovery tank 76.

FIG. 8 is a schematic depicting the layout of a surface cleaning device according to one embodiment of the present disclosure. As shown, a surface cleaning device is contemplated that comprises a sanitization tank 80, a pump 82, and a Venturi tube 84. As shown, various sensing means are provided, including pressure sensors 86a, 86b, 86c, at least one pressure gauge 88 and at least one rotameter 90 for measuring flow rate(s). As shown, fluid may be continuously recirculated from a sanitization tank 80, through a Venturi tube 84, and back to the sanitization tank 80. A filter 92 is provided, which in some embodiments comprises a high-pass filter for capturing large or coarse particulates from a fluid flow stream.

According to certain embodiments, fluid to be treated may be subjected to at least one of chemical sanitization and a sanitization process including the use of cavitation bubbles formed by a Venturi to create forces upon disruption that alter, destroy, denature, or otherwise neutralize pathogens. In preferred embodiments, fluid to be treated is subjected to a chemical cleaning agent and also subjected to cavitation bubbles by passing said fluid through an orifice plate or a Venturi tube, for example.

FIG. 9 is a schematic of a device 100 according to another embodiment of the present disclosure wherein the device 100 comprises at least one battery-powered electro-chemical cell 102 for on-board creation or modification of a cleaning agent including, for example, a Chlorine Dioxide solution generated from Sodium Chloride and Sodium Chlorite. The cell comprises a tank 104 comprising contacts 113 in communication with at least one battery 111 or other means of providing electrical energy to the electrodes 113.

In various embodiments, an electro-chemical cell 102 is provided that comprises an anode and a cathode that are both approximately 4.5 cm in diameter and spaced approximately 2.0 mm apart. The anode and/or the cathode comprise an iridium coated Titanium/Platinum alloy. In some embodiments, a current of approximately 4 amps is applied at approximately 11 Volts at a power rating of 45 Watts to generate a solution. U.S. Pat. No. 2,163,793 to Ogden and Pat. No. 2,717,237 to Rempel, which are hereby incorporated by reference in their entireties, disclose methods and systems of electrolytic production of chlorine dioxide. Various features and methods of these references are contemplated for use with floor-cleaning devices of the present disclosure.

The cleaning agent may be drawn from a generation tank 104 into either a dirty water tank or a clean solution tank 110 by way of a Venturi injector 106. In the depicted embodiment, the Venturi injector 106 does not comprise a device that is operable or intended to create cavitation bubbles. It is contemplated, however, that an additional Venturi device is provided for that specific purpose within the system shown in FIG. 9. A valve 109 is provided to control fluid flow.

FIG. 9 depicts a system wherein the electro-chemical cell 102 is operable to create or modify a fluid cleaning agent. The modified agent is then drawn into further components of a cleaning system by the operation of a Venturi 106 through which additional fluid is pumped by at least one pump 108. The combined or comingled fluid from the pump and the electro-chemical cell 102 collected in a tank 110. Fluid collected or provided in the tank 110 may be subjected to further treatment and/or dispensed for use in cleaning operations.

FIG. 10 is a schematic view of a Chlorine Dioxide removal or mitigation system 114 according to one embodiment of the present disclosure. As shown, a compressor 116 is provided to convey air 117 to a sanitization tank 118 and increase mass transfer and a rate of removal of Chlorine Dioxide through a vapor phase. An air filter 120 is provided to filter vaporized contents, and a color indicator 122 is provided in or in combination with the filter 120 to indicate to a user when the filter requires replacement. Air is exhausted to an external environment 123.

FIG. 11 is a schematic of a system 130 of the present disclosure wherein fluid from a sanitization or "scrubber tank" 131 is cycled through a Venturi tube 132 to create cavitation bubbles and provide an associated cleaning or sanitization effect. A valve 134 is provided to regulate a flow of sanitized fluid to a floor or ground surface and/or to return the fluid to the scrubber tank 131. Although not shown in FIG. 11, a cleaning agent (e.g. Chlorine Dioxide) is contemplated as being provided to enhance sanitization of the fluid. The cleaning agent may be introduced into the system or created in the system at various locations including, for example, a recovery tank wherein the agent is then passed to a sanitization tank 131. It will be recognized that dimensions and characteristics of Venturi tubes for use with embodiments of the present disclosure may vary based on user-preference, machine requirements (flow rate, for example)

and other factors. Additionally, it is contemplated that a plurality of Venturi tubes may be provided to increase sanitization and/or flow rates.

As shown in FIG. 11, a sanitization tank 131 is provided as a central repository for fluid. The sanitization tank 131 is in fluid communication with at least one pump 136, and preferably first and second pumps 136a, 136b. The sanitization tank 131 comprises an inlet that is operable to receive or collect fluid from a vacuum shoe or similar device. A filter 138 is provided to filter debris and solids from the fluid prior to entering the pump(s) 136a, 136b. The pumps are operable to transfer fluid to and through the Venturi 132, where it then passes to a relief valve 133 and to the valve 134. The valve 134 is operable to selectively control fluid flow such that the fluid may be returned or otherwise provided to a floor surface and/or be diverted back to a scrubber tank. At least one filter is provided downstream of the valve 134 to provide a final filtration stage before dispensing the fluid to a floor surface. In the depicted embodiment, a plurality of filters 140a, 140b, 140c are provided in series. It is contemplated that the filters 140a, 140b, 140c are provided as filters of decreasing pore size to sequentially filter larger then smaller particulate and prevent the finer filter(s) from becoming obstructed with large debris. One or more pressure valves 142 are provided at various points in the system 130.

FIG. 12 is a cross-sectional view of a Venturi feature 150 according to one embodiment of the present disclosure. As shown the Venturi feature 150 generally comprises a tube or fluid conduit. The Venturi feature 150 comprises an overall length L, a maximum diameter D, and a constricted diameter d. An entrance portion 152 comprises a maximum diameter D that converges in a conical convergent section 154 with a length Lcc extending between an inlet of the Venturi and a constricted throat 156. The throat 156 is connected to a conical divergent section 158 extending to an outlet 159. The throat 156 comprise a length LT extending between the convergent and divergent sections. Although the dimensions and proportions of Venturi features may vary in different embodiments of the present disclosure, one embodiment of the present disclosure contemplates a Venturi feature 150 comprising an overall length of between approximately 2.0 and 10.0 inches, and preferably of approximately 4.0 and 6.0 inches; an entrance diameter of between approximately 0.50 inches and 1.25 inches, and preferably of approximately 0.75 inches; a constricted diameter in the throat of between approximately 0.05 inches and 0.5 inches, and preferably of approximately 0.17 inches; a throat length LT of between approximately 0.05 inches and 0.5 inches, and preferably between approximately 0.17 and 0.25 inches. A length of the conical convergent section is preferably about 20 percent of the total length L. A length of the conical divergent section is preferably about 60 percent of the total length L. In preferred embodiments of the present disclosure at least one Venturi feature 150 is provided within a floor cleaning device wherein a ratio of the throat diameter d to the inlet diameter D is approximately 0.22. Applicant has found that such features and geometries provide for efficient and reliable generation of cavitation bubbles for use in cleaning operations without creating excessive or unreasonable pressure or power demands from a pump, for example.

An entrance angle α is provided in the conical convergent section, and an exit angle β. In some embodiments, the exit angle is less than the entrance angle. In various embodiments, the entrance angle α comprises an angle between approximately 5 and 15 degrees, and preferably between approximately 9 and 11 degrees. In various embodiments, the exit angle β comprises an angle between approximately 2 and 10 degrees, and preferably between approximately 3 and 7 degrees. The Venturi feature of the depicted embodiment is preferably provided with a flow rate of approximately 8 gallons per minute and a pressure of approximately 60 psi.

The strength of cavitation produced by a Venturi tube can be expressed as the Cavitation Number as follows:

$$Ca = \frac{p - p_v}{\frac{1}{2}\rho v^2}$$

As shown above, the Cavitation Number (Ca) is calculated as a ratio of the difference between downstream pressure (p) and the vapor pressure of the liquid ($p_v$) to half of the product of density of the liquid (ρ) times the square of the liquid velocity (v). In preferred embodiments, an optimal cavitation number is between approximately 0.13 and 0.17.

The exact mechanisms by which cavitation kills cells are unknown; although, studies suggest that the damaging effects of the free radicals are likely a smaller factor in cell death compared to the shock waves. The high velocity shockwaves create a volatile flow with changing pressures, eddies, and micro vorticities. When cells are exposed to these turbulent conditions they are pulled in opposite directions, creating shear stress, which increases the permeability of the outer membrane or in some cases completely disrupts it. In some embodiments, the formation of and provision of cavitation bubbles is provided in combination with the application of a chemical cleaning agent such as an Aqueous Solution wherein cavitation bubbles provide a mechanical means for breaking down or damaging cells such that the chemical agent is more effective than if it were applied to healthy, undamaged cells. Necessary dwell times and overall device effectiveness are thereby improved.

While various embodiments of the present disclosure have been described in detail, it is apparent that modifications and alterations of those embodiments will occur to those skilled in the art. Moreover, references made herein to "the present invention" or aspects thereof should be understood to mean certain embodiments of the present disclosure and should not necessarily be construed as limiting all embodiments to a particular description. It is to be expressly understood that such modifications and alterations are within the scope and spirit of the present disclosure, as set forth in the following claims.

What is claimed is:

1. A floor cleaning machine, comprising:
a chassis;
a first storage tank for holding unused cleaning fluid;
a second storage tank for holding spent cleaning fluid;
a high-pressure injection nozzle in fluid communication with an internal volume of the first storage tank, wherein the high-pressure injection nozzle is provided within an internal volume of the first storage tank and is operable to inject a pressurized fluid into the internal volume of fluid to create a shear force and form cavitation bubbles in a volume of fluid within the first storage tank; and
at least one dispensing apparatus for dispensing fluid from the first storage tank.

2. The floor cleaning machine of claim 1, wherein the high-pressure injection nozzle provides a fluid at a pressure of between approximately 800 and 4,000 PSI to the first storage tank.

3. The floor cleaning machine of claim 1, wherein a high-pressure injection nozzle is provided in the second storage tank.

4. The floor cleaning machine of claim 1, wherein at least one vacuum apparatus is in fluid communication with the second storage tank to convey used or spent fluids from a floor surface to the second storage tank.

5. The floor cleaning machine of claim 1, wherein an aqueous solution of chlorine dioxide, various alkyls, one or more various salts and tap water is provided as a concentrate on-board the device, and wherein the solution is operable to be injected into a cleaning fluid stored in at least one of the first fluid storage tank and the second fluid storage tank.

6. The floor cleaning machine of claim 1, wherein the first fluid storage tank comprises a first internal volume and a second internal volume.

7. The floor cleaning machine of claim 6, wherein a pump is provided and operable to convey fluid between the first internal volume and the second internal volume.

8. The floor cleaning machine of claim 7, further comprising a Venturi tube provided between the first internal volume and the second internal volume.

9. A floor cleaning machine, comprising:
a chassis;
a first fluid storage area and a second fluid storage area;
a pump operable to convey fluid from the first fluid storage area to the second fluid storage area;
a Venturi tube provided between the first fluid storage area and the second fluid storage area, wherein the Venturi tube is operable to receive fluid from the pump and the Venturi tube is operable to create a reduced pressure and create cavitation bubbles that are operable to clean and disinfect at least one of fluid in the machine and a surface;
at least one dispensing apparatus for dispensing fluid from the machine to a floor or ground surface;
a vacuum apparatus comprising a squeegee and at least one vacuum port provided on a lower portion of the chassis, wherein the vacuum apparatus is operable to transmit a fluid from a floor or ground surface to an interior of the chassis.

10. The floor cleaning machine of claim 9, wherein the floor cleaning machine comprises a recovery tank and the vacuum apparatus is in fluid communication with the recovery tank to convey used or spent fluids from the floor surface to the recovery tank.

11. The floor cleaning machine of claim 10, wherein a high-pressure injection nozzle is provided in the machine.

12. The floor cleaning machine of claim 9, wherein at least one of the first fluid storage area and the second fluid storage area comprises a solution comprising water, sodium chloride, and sodium chlorite.

13. A floor cleaning machine, comprising:
a chassis;
a first storage tank for holding unused cleaning fluids and a second storage tank for holding spent cleaning fluids;
a high-pressure injection nozzle provided at least partially within an internal volume of the first storage tank, and wherein the high-pressure injection nozzle is operable to inject a pressurized fluid into the unused cleaning fluids of the first storage tank to form cavitation bubbles in the unused cleaning fluids housed within the floor cleaning machine;
at least one dispensing apparatus for dispensing unused cleaning fluid from the first storage tank; and
a vacuum apparatus comprising a vacuum port proximal to a lower portion of the chassis for retrieving fluids.

14. The floor cleaning machine of claim 13, wherein the high-pressure injection nozzle provides a fluid at a pressure of between approximately 800 and 4,000 PSI.

15. The floor cleaning machine of claim 13, wherein a high-pressure injection nozzle is provided in the second storage tank.

16. The floor cleaning machine of claim 13, wherein the vacuum apparatus is in fluid communication with the second storage tank to convey used or spent fluids from a floor surface to the second storage tank.

17. The floor cleaning machine of claim 13, wherein an aqueous solution of chlorine dioxide, various alkyls, one or more various salts and tap water is provided as a concentrate on-board the device, and wherein the solution is operable to be injected into a cleaning fluid stored in at least one of the first fluid storage tank and the second fluid storage tank.

18. The floor cleaning machine of claim 13, further comprising a third fluid storage tank in selective fluid communication with at least one of the first fluid storage tank and the second fluid storage tank, and wherein the third fluid storage tank is operable to house and selectively dispense a solution to treat a fluid in the first or second fluid storage tank.

19. The floor cleaning machine of claim 18, wherein the third fluid storage tank comprises a solution comprising water, sodium chloride, and sodium chlorite.

* * * * *